US00PP27616P2

(12) United States Plant Patent
Egger

(10) Patent No.: US PP27,616 P2
(45) Date of Patent: Jan. 24, 2017

(54) ***KNIPHOFIA* PLANT NAMED 'POCO YELLOW'**

(50) Latin Name: ***Kniphofia* spp.**
Varietal Denomination: Poco Yellow

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 30 days.

(21) Appl. No.: 14/756,168

(22) Filed: Aug. 11, 2015

(51) Int. Cl.
*A01H 5/02* (2006.01)

(52) U.S. Cl.
USPC ..... Plt./443

(58) Field of Classification Search
USPC ..... Plt./443
See application file for complete search history.

(56) References Cited

PUBLICATIONS

Declaration of Janet N. Egger dated Aug. 5, 2015.

*Primary Examiner* — Keith Robinson
(74) *Attorney, Agent, or Firm* — Klarquist Sparkman, LLP; Sheree Rybak

(57) ABSTRACT

A new and distinct *Kniphofia* plant characterized by its habit of forming multiple crowns fast and each crown produces one or two inflorescences in the first season, large inflorescences of yellow flowers on short stems, a very long bloom time with repeat blooming from July through October in Canby, Oreg., a short habit, narrow, grassy leaves, and excellent vigor.

1 Drawing Sheet

Botanical denomination: *Kniphofia* spp.
Cultivar designation: 'Poco Yellow'.

BACKGROUND OF THE INVENTION

The present invention relates to a new and distinct *Kniphofia*, and given the cultivar name 'Poco Yellow'. *Kniphofia* is in the family Xanthorrhoeaceae. 'Poco Yellow' is a hybrid resulting from a planned breeding program to produce short, compact, reblooming *Kniphofia*. The cross was made using the following proprietary, unreleased plants: *Kniphofia* 41-1, as the seed parent, and an unknown yellow flowering seedling as the pollen parent. It was selected for best habit, flower color, reblooming, and crown count from many seedlings of the cross in Canby, Oreg.

Compared to *Kniphofia* 41-1, the seed parent, the new cultivar is more free-flowering and has a shorter habit.

Compared to *Kniphofia* 'Lemon Popsicle', U.S. Plant Pat. No. 24,011, the new cultivar is ⅓ shorter and has lighter yellow flowers and broader inflorescences.

SUMMARY OF THE INVENTION

The new cultivar is unique and characterized by:

1. its habit of forming multiple crowns fast and each crown produces one or two inflorescences in the first season,
2. large inflorescences of yellow flowers on short stems,
3. a very long bloom time with repeat blooming from late June through October in Canby, Oreg.,
4. a short habit,
5. narrow, grassy leaves, and
6. excellent vigor.

This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a group of 10-month-old *Kniphofia* 'Poco Yellow' in the ground in the trial field in September in Canby, Oreg.

DETAILED PLANT DESCRIPTION

The following is a detailed description of the new *Kniphofia* cultivar based on observations of 13-month-old specimens growing outside in full sun in Canby, Oreg. These were planted as 4" plants in late May. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition, 2007.

Plant:

*Type*.—Rhizomatous herbaceous perennial.
*Hardiness*.—USDA Zones 7 to 9.
*Size*.—Grows to 60 cm wide and 50 cm tall from the top of the soil to the top of the foliage.

*Crown #.*—About 50.
*# Leaves/crown.*—About 13.
*# Inflorescences/crown.*—1 to 2.
*Form.*—Clumping.

Leaf:
*Type.*—Simple.
*Shape.*—Strap-like, keeled.
*Arrangement.*—Basal rosette.
*Blade size.*—39 cm to 60 cm long and 10 mm to 20 mm wide.
*Margins.*—Entire.
*Apex.*—Acuminate.
*Base.*—Clasping.
*Surface texture.*—Glabrous on both surfaces.
*Venation.*—Parallel.
*Color.*—Top and bottom side Green 137A.

Inflorescence:
*Type.*—Spike-like scapose raceme.
*Number of flowers per raceme.*—Up to 220.
*Inflorescence.*—15 cm long and 5 cm to 6 cm wide.
*Peduncle description.*—Grows to 45 cm long and 8 mm wide, glabrous, Yellow Green 146B.
*Pedicle description.*—1.5 mm long, glabrous, Yellow Green 146A.
*Bloom time.*—June through October in Canby, Oreg.
*Lastingness.*—An inflorescence lasts for 2 to 4 weeks depending on the temperature.

Flower bud:
*Size.*—27 mm long and 5 mm wide.
*Shape.*—Cylindrical.
*Surface texture.*—Glabrous.
*Color.*—From Yellow Orange 16B on the younger buds lightening to Yellow 12B on older buds.

Flower:
*Type.*—Actinomorphic.
*Shape.*—Cylindrical and tubular.
*Size.*—Grows to 29 mm deep and 6 mm wide.
*Texture.*—Waxy.
*Surface texture.*—Glabrous on both sides.
*Corolla description.*—27 mm long and 6 mm wide, 6-lobed fused tepals, tube 24 mm long and 5 mm wide, lobes each 3 mm wide and 3 mm long, ovate, entire, obtuse to acute, inside and out: Yellow 11B with Green Yellow 146C on end nearest the stem on the main veins.
*Pistil description.*—One, 29 mm long, ovary 3 mm long 2 mm wide, Yellow Green 146C, style 25 mm long, Yellow 8C, stigma White NN155A.
*Stamen.*—6, 21 mm long, filaments 20 mm long, Yellow 8C, anthers 1 mm long and Yellow 13A tinted on backs Greyed Orange 186A, pollen none.
*Fragrance.*—None.

Fruit: A few fruits are formed, but do not fully develop.

Seed: None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

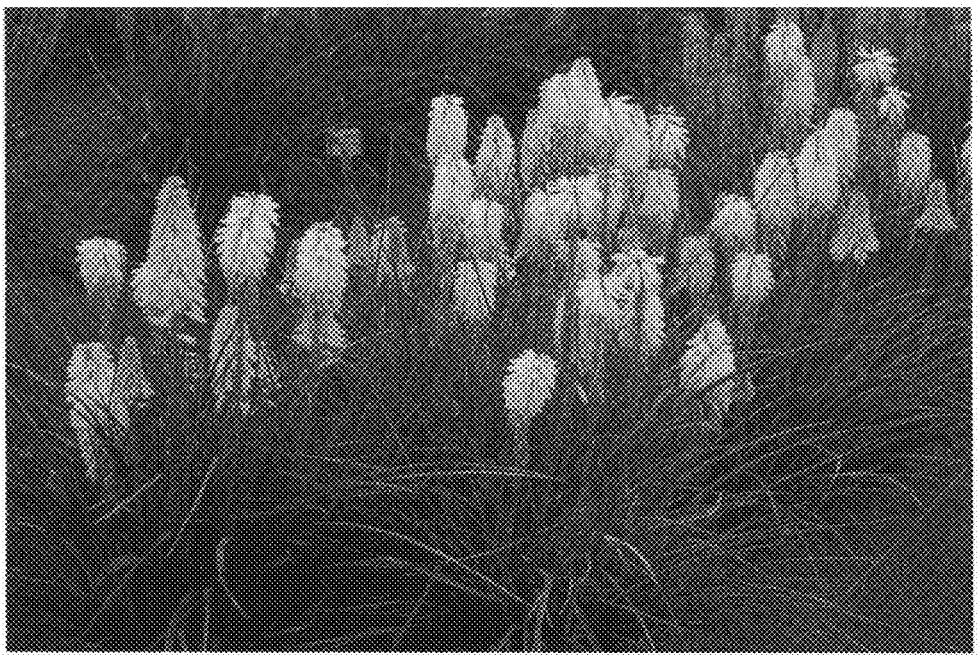

* * * * *